United States Patent [19]

Huth et al.

[11] Patent Number: 5,356,555
[45] Date of Patent: Oct. 18, 1994

[54] NON-OXIDATIVE METHOD AND COMPOSITION FOR SIMULTANEOUSLY CLEANING AND DISINFECTING CONTACT LENSES USING A PROTEASE WITH A DISINFECTANT

[75] Inventors: Stanley W. Huth, Newport Beach; Sam W. Lam, Laguna Niguel; Abraham M. Espiritu, Oceanside, all of Calif.

[73] Assignee: Allergan, Inc., Irvine, Calif.

[21] Appl. No.: 944,567

[22] Filed: Sep. 14, 1992

[51] Int. Cl.$^5$ .................. A61L 2/16; C11D 3/386; C11D 3/48; G02C 13/00

[52] U.S. Cl. ................ 252/106; 252/174.12; 252/DIG. 12; 514/839; 514/840; 514/912; 422/28; 422/37

[58] Field of Search .......... 252/106, 174.12, DIG. 12; 514/839, 840, 912; 422/28, 37

[56] References Cited

U.S. PATENT DOCUMENTS

| Re. 32,672 | 5/1988 | Huth | 252/95 |
|---|---|---|---|
| 4,029,817 | 6/1977 | Blanco | 424/329 |
| 4,250,269 | 2/1981 | Buckman | 525/6 |
| 4,407,791 | 10/1983 | Stark | 424/80 |
| 4,525,346 | 6/1985 | Stark | 424/80 |
| 4,758,595 | 11/1984 | Ogunbiyi | 514/635 |
| 4,820,447 | 4/1989 | Medcalf | 252/117 |
| 4,996,059 | 2/1991 | Grollier | 252/547 |
| 5,073,292 | 12/1991 | Hessel | 252/174.12 |
| 5,096,607 | 3/1992 | Mowrey-McKee | 252/106 |

FOREIGN PATENT DOCUMENTS

| 349487 | 1/1990 | European Pat. Off. . |
| 359574 | 3/1990 | European Pat. Off. . |
| 384666 | 8/1990 | European Pat. Off. . |
| 0456467-A2 | 8/1991 | European Pat. Off. . |
| 4945012 | 5/1982 | Japan . |
| 63-068514A | 3/1988 | Japan . |
| WO9109523 | 7/1991 | PCT Int'l Appl. . |
| WO9215334 | 9/1992 | PCT Int'l Appl. . |

*Primary Examiner*—Dennis Albrecht
*Attorney, Agent, or Firm*—Spensley Horn Jubas & Lubitz

[57] ABSTRACT

A method for simultaneously cleaning and disinfecting contact lenses includes forming a disinfection solution containing an ophthalmically safe amount of a disinfecting agent, such as polyhexamethylene biguanide, and providing an effective amount of a proteolytic enzyme, such as subtilisin A. The disinfecting agent and proteolytic enzyme are selected such that in the working solution, the disinfection efficacy of the disinfecting agent is at least maintained. Preferably, after cleaning and disinfection, the lens can be rinsed with the disinfection solution, whereby the lens may then be directly inserted in the eye of the contact lens user without further rinsing.

8 Claims, No Drawings

NON-OXIDATIVE METHOD AND COMPOSITION FOR SIMULTANEOUSLY CLEANING AND DISINFECTING CONTACT LENSES USING A PROTEASE WITH A DISINFECTANT

BACKGROUND OF THE INVENTION

1. Field of the Invention

This invention relates to a method for simultaneously cleaning and disinfecting contact lenses and compositions for the same. More specifically, the present invention is directed to a non-oxidative method for simultaneously cleaning and disinfecting contact lenses by soaking the lenses in an aqueous solution containing a disinfecting agent to which is added a proteolytic enzyme.

2. Description of Related Art

The growth of the contact lense industry has led to a dramatic increase in the number of lenses and care regimens in the marketplace. Designing care regimens to meet the needs of all possible permutations has become a challenge to the industry. In particular, a goal of the lens care industry is to simplify the lens care regimen to obtain greater patient compliance.

In the normal course of wearing contact lenses, tear film and debris consisting of proteinaceous, oily, sebaceous, and related organic matter have a tendency to deposit and build up on lense surfaces. As part of the routine care regimen, contact lenses must be cleaned to remove these tear film deposits and debris. If these deposits are not properly removed, both the wetability and optical clarity of the lenses is substantially reduced causing discomfort for the wearer.

The only safe and effective means found to date for removing protein build-up is the use of enzymes, whose hydrolytic activity reduces the proteinaceous materials to small, water soluble subunits. Particularly useful are proteolytic enzymes or proteases. U.S. Pat. No. 3,910,296 discloses the use of proteases for cleaning contact lenses.

Further, contact lenses, especially those made from hydrophilic materials, must be continuously disinfected to kill any harmful microorganisms that may be present or grow on the lenses. Microorganisms that are incorporated in the panel of microorganisms required by the 1985 U.S. FDA guidelines for contact lens solutions for disinfection efficacy include *Serratia marcescens* ("S.M.") (ATCC 14041), *Staphylococcus epidermidis* ("S.E.") (ATCC 17917), *Pseudomonas aeruginosa* ("P.A.") (ATCC 15442) and *Candida albicans* ("C.A.") (ATCC 10231).

A number of methods for disinfecting contact lenses have been used such as the use of high temperatures, the use of oxidative chemicals, and the use of antimicrobial agents. U.S. Pat. Nos. 4,407,791 and 4,525,346 show the polyquaternary ammonium contact lens disinfecting agent 1-tris (2-hydroxyethyl) ammonium-2-butenyl-4-poly [1-dimethyl ammonium-2-butenyl]-w-tris (2-hydroxyethyl) ammonium chloride salt. European patent application 89810477.3 shows the disinfecting agent dodecyl-dimethyl-(2-phenoxyethyl)-ammonium bromide. U.S. Pat. No. 4,029,817 assigned to Allergan, Inc. shows the contact lens disinfecting agent tallow triethanol ammonium chloride. U.S. Pat. No. 4,758,595 shows the hexamethylene biquanide contact lens disinfecting agent.

In addition to cleaning and disinfecting, contact lenses must also be rinsed. A typical solution for rinsing is a normal saline solution. If the lenses are inserted in the eye without first rinsing, the eyes will burn and can become seriously irritated.

New methods have been developed which can remove proteinaceous material from contact lenses while disinfecting the lenses. For example, U.S. Pat. No. 4,614,549 discloses a single-step method of cleaning and disinfecting contact lenses in aqueous solutions of proteolytic enzymes at temperatures of between 60° C. and 100° C. This method requires the use of electrical disinfecting apparatus and elevated temperatures. U.S. Pat. Re. 32,672 assigned to Allergan, Inc. discloses a method by which the lenses are immersed in a solution containing peroxide and a peroxide-active enzyme. Japanese patent application Showa 49-45012 discusses cleaning and sterilizing contact lenses by contacting the lens with an aqueous solution containing a protease and sterilizing agent such as triethanol tallow ammonium chloride, thimerosal and a wide range of reducing agents. U.S. Pat. No. 5,096,607 discloses a method for simultaneously cleaning and disinfecting contact lenses by contacting the lenses with a solution containing a proteolytic enzyme and either a polymeric quaternary ammonium salt or a biguanide and adjusting the osmotic value of the solution to a level which does not inhibit the activity of the quaternary ammonium salt or the biguanide. This patent describes a wide range of useful proteolytic enzymes (in kind and amount) and a wide range of quaternary ammonium salts and biguanides (in kind and amount). All of the simultaneous cleaning and disinfecting methodologies typically require the step of rinsing the cleaned and disinfected lenses.

SUMMARY OF THE INVENTION

It has unexpectedly been discovered that not all combinations of proteolytic enzymes and antimicrobial agents provide adequate disinfection efficacy. It has been found that for some combinations of proteolytic enzyme and antimicrobial agent, the disinfection efficacy is significantly adversely affected.

According to the present invention, a non-oxidative method for simultaneously cleaning and disinfecting contact lenses is provided comprising combining the lenses with a multipurpose non-irritating aqueous solution containing a disinfecting agent and a proteolytic enzyme for a time sufficient to clean and disinfect the lenses. The disinfecting agent and proteolytic enzyme are chosen such that when combined, the disinfecting efficacy of the disinfecting agent is at least maintained Preferably, after the lens is cleaned and disinfected, the same multipurpose solution used to disinfect can be used to rinse the lens. The lens can thereafter be placed directly in the contact lens user's eye, without any further rinsing. Thus in one aspect the present invention solves the long felt need of providing a single multipurpose solution for use in a lens care regimen. And in another aspect, the present invention solves the long felt need of providing a combined disinfecting agent/-proteolytic enzyme solution wherein the disinfection efficacy of the disinfecting agent is at least maintained.

DETAILED DESCRIPTION OF THE INVENTION

The present invention can be used with all contact lenses such as conventional hard, soft, rigid, gas permeable, and silicone lenses but is preferably employed with soft lenses such as those commonly referred to as hydrogel lenses prepared from monomers such as hydroxyethylmethacrylate, hydroxyethylmethylmethacrylate, vinylpyrrolidone, glycerolmethacrylate, methacrylic acid or acid esters and the like. Hydrogel lenses typically absorb significant amounts of water such as from 38 to 80 percent by weight.

Generally, these cleaning and disinfecting solutions are prepared by mixing two components, i.e., dissolving the enzyme preferably in tablet form in a solution containing the disinfecting agent. However, other methods of combining the active components as well as off the shelf compositions containing all of the active components are contemplated as being within the scope of this invention.

The proteolytic enzymes used herein must have at least a partial capability to hydrolyze peptide-amide bonds which reduces the proteinaceous material to smaller water-soluble subunits. Typically, these enzymes will exhibit some lipolytic, amylolytic or related activities associated with the proteolytic activity and may be neutral, acidic or alkaline. In addition, separate lipases or carbohydrases may be used in combination with the proteolytic enzymes as well as thermally stable proteases.

A thermally stable protease or thermophilic enzyme denotes a protease that is stable and active at temperatures higher than 70° C. or even higher than 100° C. One such heat stable protease is thermolysin. Reference may be had to pages 642–650 of Perlmann et al., "Proteolytic Enzymes," Methods in Enzymology, Volume XIX, Academic Press (1970).

Examples of suitable proteolytic enzymes include but are not limited to pancreatin, trypsin, chymotrypsin, collagenase, keratinase, carboxylase, papain, bromelain, aminopeptidase, Aspergillo peptidase, pronase E (from *S. griseus*) and dispase (from Bacillus, polymyxa) and mixtures thereof. If papain is used, it is also necessary to use a reducing agent and a chelating agent, both of which are discussed below.

The preferred group of proteolytic enzymes are the microbial derived enzymes such as those derived from Bacillus, Streptomyces, and Aspergillus microorganisms. Most preferred are the Bacillus derived alkaline proteases generically called subtilisin enzymes. Microbial derived enzymes are disclosed in U.S. Pat. No. 4,690,773 incorporated herein by reference.

Reference is also made to Keay, L, Moser, PW and Wildi, BS, "Proteases of the Genus Bacillus. II Alkaline Proteases," Biotechnology and Bioengineering, Vol. XII, pp. 213–249 (1970) and Keay, L and Moser, PW, "Differentiation of Alkaline Proteases from Bacillus Species", Biochemical and Biophysical Research Comm., Vol. 34, No. 5, pp. 600–604 (1969). Metalloproteases, those enzymes which contain a divalent metal ion such as calcium, magnesium or zinc bound to the protein, may also be used.

The subtilisin enzymes include two sub-classes, subtilisin A and subtilisin B. In the subtilisin A grouping are enzymes derived from such Species as *B. subtilis, B. licheniformis* and *B. pumilis*. Organisms in this sub-class produce little or no neutral protease or amylase. The subtilisin B sub-class includes enzymes from such organisms as *B. subtilis, B. subtilis* var. *amylosacchariticus, B. amyloliquefaciens* and *B. subtilis* NRRL B3411. These organisms produce neutral proteases and amylases on a level about comparable to their alkaline protease production. Generally, the preferred enzymes are active proteolytic enzymes, with the most preferred being subtilisin A.

The identification, separation and purification of enzymes is an old art. Many identification and isolation techniques exist in the general scientific literature for the isolation of enzymes, including those enzymes having proteolytic and mixed proteolytic/amylolytic or proteolytic/lipolytic activity. The enzymes contemplated by this invention can be readily obtained by known techniques from plant, animal or microbial sources.

With the advent of recombinant DNA techniques, it is anticipated that new sources and types of stable proteolytic enzymes will become available. Such enzymes should be considered to fall within the scope of this invention so long as they meet the criteria for stability and activity set forth herein, See Japanese Laid Open Application No. J6 0030-685 for one example of the production of proteases by recombinant DNA from *Bacillus subtilis*.

The present invention generally employs an effective and efficacious amount of enzyme to clean the lenses. An effective and efficacious amount is that which removes a substantial portion of the proteinaceous deposits which occur during normal wear in a reasonable time and which does not decrease the disinfection efficacy of the disinfecting agent when the enzyme and disinfecting agent are combined in the working solution. The precise amount of enzyme required to make an effective and efficacious cleaner will depend on several factors including the activity of the enzyme, the purity of the enzyme, the amount of proteinaceous matter deposited on the lenses, the desired soaking period, the nature and concentration of the disinfecting agent, the specific the of lenses, as well as other well known factors.

The working solution should contain sufficient enzyme to provide between about 0.0001 to 0.5 Anson units per single lens treatment, preferably between 0.0008 and 0.036, more preferably between 0.0010 and 0.012, optimally 0.002, Anson units per single lens treatment, in a 2–10 mL soak volume. Enzyme concentrations lower than these stated here probably will serve to clean the lens if sufficient time and heat is provided but such time may be so long and such heat so high as to be practically not useful in a usual lens cleaning and disinfecting regimen. The precise amount of enzyme will vary with the purity of the enzyme and will need to be finally determined on a lot-by-lot basis.

Enzyme activity is pH dependent. For any given enzyme, there will be a particular pH range in which that enzyme will function best. The determination of such range can readily be done by known techniques. It is preferred to manipulate the working solution to an optimum pH range for a given enzyme but such is not an absolute requirement. Generally, it is preferred that the enzyme be selected to have substantial activity at a pH between 6.5 and about 9.5 and even more preferably at between 6.9 to 7.9.

The enzyme may be employed in liquid or solid form in combination with a reducing agent and additional components. Preferably, the enzymes and other agents are provided in solid form such as tablets or powders which are mixed with the aqueous multipurpose disinfecting solutions discussed below.

A reducing agent may be present in the working solution and in such case would preferably be incorporated into the enzyme tablet. The reducing agent is generally any non-toxic reducing agent, either dry or liquid, depending in part upon whether the delivery system is tablet or solution. Although thiols are preferred and N-acetylcysteine more preferred, reducing agent sources generally include SH (group)-containing water-soluble lower alcohols, organic carboxylic acids, organic amines and salts thereof, amino acids and di- or tripeptides, e.g. cysteine hydrochloride ethyl ester, glutathione, homocysteine, carbamoyl cysteine, cysteinylglycine, 2-mercaptopropionic acid, 2-mercaptopropionylglycine, 2-mercaptoethylamine hydrochloride, cysteine, beta mercaptoethanol, cysteine hydrochloride, dithiothreitol, dithioerythritol, sodium bisulfate, sodium metabisulfite, thio urea, sulfites, pyrosulfites and dithionites such as the alkali metal salts or alkaline earth metal salts of sulfurous acid, pyrosulfurous acid and dithionious acid, e.g. lithium, sodium, calcium and magnesium salts and mixtures thereof.

In general, in weight to volume terms, the reducing agent will be used in amounts between 0.05% to 10% of the final working solution, with 0.3% to 1.5% preferred and 0.3% to 0.5% optimal. With the most preferred reducing agent, N-acetylcysteine, used with from 0.0008 to 0.036 Anson units of subtilisin A, the range is preferably from 0.1% to 1.0% (w/v).

Additional components may be added to or incorporated into the enzyme tablets or liquid, or working solution, which do not substantially decrease the activity of the enzyme or disinfecting agent in the working solution. For example, components such as effervescing agents, stabilizers, buffering agents, chelating and/or sequestering agents, coloring agents, tonicity adjusting agents, surfactants and the like can be employed. In addition, binders, lubricants, carriers, and other excipients normally used in producing tablets may be incorporated into the enzyme tablet when enzyme tablets are employed.

Examples of suitable buffering agents which may be incorporated into an enzyme tablet or working solution include, but are not limited to, alkali metal salts such as potassium or sodium carbonates, acetates, borates, phosphates, citrates and hydroxides, and weak acids such as acetic and boric acids. Other buffers include amino acid buffers and tromethamine, also known as 2-amino-2-hydroxymethyl-1,3-propanediol. Preferred buffering agents are alkali metal borates such as sodium or potassium borates. Additionally, other pH adjusting agents may be employed such as inorganic acids. For example, hydrogen chloride may be employed in concentrations suitable for ophthalmic uses. Generally, buffering agents are present in amounts from about 0.01 to about 2.5% (w/v) and preferably, from about 0.5 to about 1.5% (w/v), of the working solution.

Effervescing agents are typically employed when the enzyme is provided in solid form. Examples of suitable effervescing agents include, but are not limited to, tartaric or citric acid used in combination with a suitable alkali metal salt such as sodium carbonate.

The tonicity adjusting agent which may be a component of the disinfecting solution and may optionally be incorporated into an enzyme tablet is employed to adjust the osmotic value of the final cleaning and disinfecting solution to more closely resemble that of human tears and to maintain a suitable level for optimum activity by the antimicrobial agent.

Suitable surfactants can be either cationic, anionic, nonionic or amphoteric. Preferred surfactants are neutral or nonionic surfactants which may be present in amounts up to 5% (w/v). Examples of suitable surfactants include, but are not limited to, polyethylene glycol esters of fatty acids, polyoxypropylene ethers of $C_{12}$-$C_8$ alkanes, polyoxyethylene, polyoxypropylene block copolymers of ethylene diamine (i.e., poloxamine), polyoxypropylene-polyoxyethylene glycol nonionic block polymers (i.e., Pluronic polyols such as Pluronic F-127) and p-isooctylpolyoxyethylene phenol formaldehyde polymers (i.e., Tyloxapol).

Examples of preferred chelating agents include ethylenediaminetetraacetic acid (EDTA) and its salts (disodium) which are normally employed in amounts from about 0.025 to about 2.0% (w/v). Other known chelating (or sequestering agents) such as certain polyvinyl alcohols can also be employed.

The binders and lubricants for enzyme tableting purposes and other excipients normally used for producing powders, tablets and the like, may be incorporated into enzyme tablet formulations.

As used herein, disinfecting agents are defined as non-oxidative organic chemicals which derive their activity through a chemical or physiochemical interaction with the organisms. Suitable disinfecting agents are those generally employed in ophthalmic applications and include, but are not limited to, quaternary ammonium salts used in ophthalmic applications such as poly[(dimethylimino)-2-butene-1,4-diyl chloride, α-[4-tris(2-hydroxyethyl) ammonium-2-butenyl-w-tris(2-hydroxyethyl)ammonium]-dichloride (chemical registry number 75345-27-6) generally available as polyquaternium 1 ® from ONYX Corporation, benzalkonium halides, and biguanides such as salts of alexidine, alexidine free base, salts of chlorhexidine, hexamethylene biguanides and their polymers. See U.S. Pat. No. 4,758,595 incorporated herein by reference.

The salts of alexidine and chlorhexidine can be either organic or inorganic and are typically disinfecting nitrates, acetates, phosphates, sulphates, halides and the like. Generally, the hexamethylene biguanide polymers, also referred to as polyaminopropyl biguanide (PAPB), have molecular weights of up to about 100,000. Such compounds are known and are disclosed in U.S. Pat. No. 4,758,595.

Another compound which meets the foregoing criteria when detoxified is a compound having structural Formula A. See U.S. Pat. No. 4,029,817 assigned to Allergan, Inc. which is incorporated herein by reference.

Formula A wherein R is an alkyl or alkenyl radical having 12–20 carbon atoms and preferably a tallow radical, i.e., composed of mixtures of —$C_{17}H_{34}$ and —$C_{17}H_{35}$; and $R_1$, $R_2$, and $R_3$ are the same or different and represent alkyl radicals having 1–3 carbon atoms. This compound should be used together with a detoxifying amount of a non-toxic compound selected from the group consisting of water soluble polyhydroxyethyl methacrylate, carboxymethylcellulose, non-ionic surfactants such as polyoxyethylene sorbitan fatty acid esters and polyoxyethylene ethers, polyvinylpyrrolidone, polyvinyl alcohol, hydroxypropylmethylcellulose and mixtures thereof.

The preferred compound of the above Formula A is alkyl triethanol ammonium chloride wherein the alkyl group is a tallow radical. This compound is known as Miramine TA-30 ® and is commercially available from the Miranol Chemical Company. The preferred compound can be obtained as a 30% aqueous acidic solution. The compound is fairly stable in acidic pH but tends to precipitate out of solution as the base under alkaline conditions.

The compounds which act to detoxify the active ingredient of the above Formula A, yet allow the active ingredient to retain its bactericidal properties, are one or more of the following detoxifying compounds: water soluble polyhydroxyethyl methacrylate, carboxymethylcellulose, non-toxic, non-ionic surfactants, polyvinylpyrrolidone, polyvinyl alcohol and hydroxypropylmethylcellulose. The preferred compounds are the water soluble polyhydroxyethylmethacrylate, sodium carboxymethylcellulose and the non-toxic, non-ionic surfactants such as polyoxyethylene (20) sorbitan monooleate or Polysorbate 80, also known as "Tween 80."

The water soluble polyhydroxyethylmethacrylate described above is soluble in alkaline water, the solubility varying with the alkalinity of the water and also on the degree of polymerization. The preferred grade is the polymer with an average molecular weight of about 60,000 to 700,000 and preferably having an average molecular weight of about 80,000 to 225,000. These polymers are available from Hydron Laboratories, e.g. under the trademark "Hydron Biomedical Polymer, Type A1."

Carboxymethylcellulose or sodium carboxymethylcellulose is a synthetic cellulose gum containing 0.4 to 1.5 sodium carboxymethyl groups (—CH$_2$COONa) per glucose unit of the cellulose. It is a white, odorless, non-toxic hydroscopic powder readily dispersible in hot or cold water. The pH of a 1% solution is 6.5–8.0.

The detoxifying agents which are described as non-toxic, non-ionic surfactants are surfactants such as the polyoxyethylene sorbitan fatty acid ester, e.g. the "Tween" series of surfactants, as exemplified by Polysorbate 80; and polyoxyethylene ethers, e.g. the "Brij"-series of surfactants, as exemplified by "Brij 57". Polysorbate 80, otherwise described as polyoxyethylene (20% sorbitan monooleate) is an oleate ester of sorbitol and its anhydrides copolymerized with approximately 20 moles of ethylene oxide for each mole of sorbitol and sorbitol anhydrides. Polysorbate 60 is available commercially from Atlas Chemical Company under the name "Tween 80". "Brij 56, " also a trade name of Atlas Chemical Company, is polyoxyethylene (20) cetyl ether. The other well-known members of the "Tween" and "Brij" series of surfactants may also be used in the present invention.

The amount of the detoxifying compounds which may be used in connection with the disinfecting agent of Formula A varies from about 0.0001 to about 2.0% (w/v) and preferably from about 0.04 to about 0.4% (w/v) of the aqueous working solution.

Another disinfecting agent is the poly quaternary amine Croquat L. Croquat L is a quaternary ammonium substituted polypeptide which is based on a collagen hydrolysate of relatively low molecular weight, includes lauryl trimethyl ammonium chloride groups and has a molecular weight in the range of 500 to about 5000. Croquat L is commercially available from Croda, Inc.

A useful quaternary ammonium substituted polypeptide disinfecting agent has the following formula

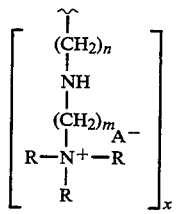

wherein the wavy line represents a polypeptide backbone; n is an integer in the range of 1 to about 5, preferably 2; m is an integer in the range of 1 to about 30, preferably about 10 to about 20; each R is independently selected from alkyl groups containing 1 to about 20 carbon atoms; A$^-$ is selected from ophthalmically acceptable anions; and x represents the number of bracketed groups interspersed along the polypeptide backbone and is an integer in the range of 1 to about 20, preferably about 2 to about 6. In one embodiment, at least one R is methyl and one other R contains about 8 to about 20 carbon atoms. In another embodiment, each of the Rs is methyl, and m is in the range of about 10 to abut 20.

Examples of ophthalmically acceptable anions include chloride (Cl$^-$), bromide, iodide, sulfate, bisulfate, phosphate, acid phosphate, nitrate, acetate, maleate, fumarate, oxalate, lactate, tartrate, citrate, gluconate, saccharate, p-toluene sulfonate and the like. The preferred ophthalmically acceptable anion is Cl$^-$.

Yet still another group of disinfecting agents are water soluble cationic polymers (WSCP). The presently useful water soluble cationic polymers preferably have the following repeating unit

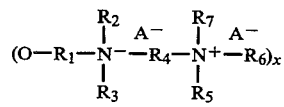

wherein R$_1$, R$_4$ and R$_6$ are each independently selected from alkylene radicals containing 1 to about 6 carbon atoms, R$^2$, R$_3$, R$_5$ and R$_7$ are each independently selected from alkyl radicals containing 1 to about 6 carbon atoms, each A$^-$ is independently selected from ophthalmically acceptable anions, and x is the number of repeating units in the polymer and is an integer in the range of about 5 to about 30. A particularly useful quaternary ammonium polymer has the following repeating unit

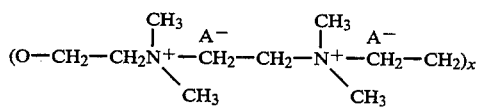

The number of repeating units per polymer molecule, represented by x, is more preferably about 8 to about 30, especially about 14.

Examples of ophthalmically acceptable anions include chloride (Cl$^-$), bromide, iodide, bisulfate, phosphate, acid phosphate, nitrate, acetate, maleate, fumarate, oxalate, lactate, tartrate, citrate, gluconate, saccharate, p-toluene sulfonate and the like. The preferred ophthalmically acceptable anion is Cl$^-$.

In one particularly useful embodiment, the quaternary ammonium polymer has a molecular weight in the range of about 500 to about 5000.

A specific example is poly [oxyethylene (dimethyliminio) ethylene - (dimethyliminio) ethylene dichloride] ("WSCP(1)") as shown in below.

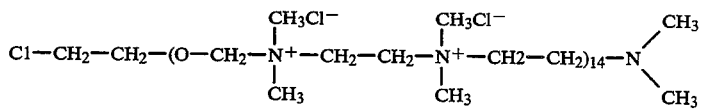

WSCP disinfecting agents are commercially available from Buckman Laboratories, Inc. and are described in U.S. Pat. No. 4,250,269 which is incorporated herein by this reference.

Other disinfecting agents include dodecyl-dimethyl-(2-phenoxyethyl)-ammonium bromide.

A disinfecting and efficacious amount of a disinfecting agent is an amount which will at least partially reduce the microorganism population in the solutions employed and wherein when combined in the working solution with the effective and efficacious amount of the proteolytic enzyme, the disinfection efficacy of the disinfecting agent is at least maintained. Preferably, a disinfecting and efficacious amount is that which will reduce the microbial burden by two log orders in four hours and more preferably by one log order in one hour for all organisms with the exception of A. fumigatus. Most preferably, a disinfecting and efficacious amount is an amount which will eliminate the microbial burden on a contact lense when used in a contact lens care regimen which includes a recommended soaking time (FDA Chemical Disinfection Efficacy Test-July, 1985 Contact Lens Solution Draft Guidelines incorporated herein). Typically, disinfecting agents are present in the working solution in concentrations ranging from about 0.00001 to no more than 0.01% (w/v). The preferred range for polyquads and biguanides is 0.00005 to 0.0015 and for WSCP and Croquat is from 0.003 to 0.015.

More preferably the agent is present in the working solution at an ophthalmically safe concentration such that the user can rinse the lens with the solution and thereafter directly place the lens in the eye.

For purposes of the present invention an aqueous solution containing from 0.00001% to less than or equal to 0.005% (w/v) of the disinfecting agent may be used as a multipurpose solution. That is, the solution can be used for disinfection, cleaning (together with an enzyme), storage and rinsing. Thus by using the methodology of the present invention, the user only needs to have proteolytic enzyme tablets and a single solution bottle. There is no longer a need for a separate saline solution bottle.

It has surprisingly been found that when the proteolytic enzyme component of the present invention is combined in the working solution with the disinfecting agent of the present invention, the disinfection efficacy of the disinfecting agent is at least maintained. As discussed in more detail below, the log kill for certain organisms does not significantly decrease but rather is substantially maintained. Thus, the enzyme and disinfecting agent formulations should be chosen such that they meet this criteria.

During practice of this invention, the enzyme formulation, either in solid or liquid form, is usually dissolved in a predetermined amount of the disinfecting solution, typically 5-10 mL where a lens vial is used or 0.8 to 3.5 mL where the lens well of a lens case is used. The solution may be isotonic or hypotonic. This solution is then contacted with lenses at ambient temperatures for a sufficient time to clean and disinfect for safe use in the eye.

In a preferred embodiment of the invention, an enzyme tablet is dissolved in an aqueous thimerosal-free multipurpose and disinfecting agent solution containing WSCP as the disinfecting agent. The lenses are then contacted with the resulting cleaning and disinfecting solution, preferably by being immersed therein, and remain in contact with the solution for a sufficient period of time to clean and disinfect the lenses. Typically, the cleaning and disinfecting will take less than about eight hours with about 1 to about 4 hours being preferred.

Preferably, the lenses can be removed from the solution and placed directly into the eye without the need for a separate neutralizing step. The lenses are rinsed with the same aqueous multipurpose and disinfecting agent solution containing the disinfecting agent prior to insertion into the eye. There is preferably no need for a separate saline solution rinsing. Thus the multipurpose and disinfecting agent solution is preferably ophthalmically acceptable, i.e., it can be placed into a human eye without causing any substantial damage or harm.

The method of sequence of combining the components to make up the solution which contacts the lenses will vary with the physical characteristics of the components employed; but the order of addition is not critical to the practice of this invention. For example, the enzyme could be separately formulated as tablets or powders.

It is most convenient to formulate the enzyme and other dry components as a powder or tablet and to dissolve such material in the multipurpose disinfecting agent solution, then introduce the lenses into this solution. The lenses could already be in the multipurpose disinfecting agent solution when the enzyme (in aqueous form) is introduced. However practical considerations make the first method the preferred one.

The following detailed Examples 1–5 are presented to illustrate tablet compositions for the enzymatic cleaning agent component of the present invention that can be used with the multipurpose disinfecting agent solutions discussed in more detail below. These examples however are not to limit the scope of the enzymatic cleaning agent component of the present invention.

| Ingredient | Mg/Tablet |
|---|---|
| Subtilisin A | 1.042* |
| Di-Pac** | 40.0 |
| Polyethylene glycol 3350 | 4.0 |
| Povidone, PVP k-30 polyvinylpyrrolidone | 4.0 |

*Subtilisin A MG 1.5 (Novo Industries of Copenhagen, Denmark) 1.9 Au/g; 0.00198 Au/Tablet incl. 10% overage
**Di-Pac is a compressible sugar. It is comprised of 97 w/w% sucrose and 3 w/w% maltodextrin. Di-Pac is available from Amstar Sugar Corporation and is distributed by Austin Chemical Co. in Illinois.

EXAMPLE 2

| Ingredient | Mg/Tablet |
|---|---|
| Subtilisin A | 1.089* |
| Di-Pac** | 40.0 |
| Sodium carbonate, anhydrous | 2.0 |
| Polyethylene glycol 3350 | 4.0 |
| Povidone, PVP k-30 | 4.0 |

*Subtilisin A MG 1.5 (Novo Industries of Copenhagen, Denmark) 1.9 Au/g; 0.00207 Au/Tablet incl. 15% overage
**Di-Pac is a compressible sugar. It is comprised of 97 w/w% sucrose and 3 w/w% maltodextrin. Di-Pac is available from Amstar Sugar Corporation and is distributed by Austin Chemical Co. in Illinois.

EXAMPLE 3

| Ingredient | Mg/Tablet |
|---|---|
| Subtilisin A | 0.4* |
| N-acetylcysteine | 30.0 |
| Sodium carbonate, anhydrous | 52.0 |
| Sorbitol, FG instant | 40.0 |
| Polyethylene glycol 3350 | 6.0 |
| Tartaric acid | 7.0 |

*Subtilisin A, 30 Au/g (Novo Industries of Copenhagen, Denmark)

EXAMPLE 4

| Ingredient | Mg/Tablet |
|---|---|
| Subtilisin A | 0.1* |
| N-acetylcysteine | 7.50 |
| Sodium carbonate, anhydrous | 13.0 |
| Sorbitol, FG instant | 10.0 |
| Polyethylene glycol 3350 | 1.5 |
| Tartaric acid | 1.75 |

*Subtilisin A, 30 Au/g (Novo Industries of Copenhagen, Denmark)

EXAMPLE 5

| Ingredient | Mg/Tablet |
|---|---|
| Subtilisin A | 0.08* |
| N-acetylcysteine | 6.00 |
| Sodium carbonate, anhydrous | 10.40 |
| Sorbitol, FG instant | 8.00 |
| Polyethylene glycol 3350 | 1.20 |
| Tartaric acid | 1.40 |

*Subtilisin A, 30 Au/g (Novo Industries of Copenhagen, Denmark)

The following detailed Examples 6-8 are presented to illustrate multi-purpose disinfecting agent solutions, but are not to limit the scope of the disinfecting agent component of the present invention.

EXAMPLE 6

| Ingredient | % w/v |
|---|---|
| Polyhexamethylene biguanide, Cosmocil CQ | 0.0001 |
| Edetate disodium USP | 0.05 |
| Sodium chloride USP | 0.37 |
| Tromethamine | 1.20 |
| Tyloxapol USP | 0.025 |
| Hydrochloric acid | Adjust to pH 7.5 |

EXAMPLE 7

| Ingredient | % w/v |
|---|---|
| Hydroxyethyl cellulose, NF | 0.65 |
| Sodium chloride, USP | 0.67 |
| Boric acid, NF | 0.39 |
| Sodium borate decahydrate, NF | 0.20 |
| Edetate disodium, USP | 0.127 |
| WSCP | 0.006 |
| Croquat L | 0.010 |

EXAMPLE 8

| Ingredient | % w/v |
|---|---|
| WSCP | 0.003 |
| Boric acid | 0.39 |
| Edetate disodium | 0.1 |
| Sodium chloride | 0.40 |
| Sodium borate decahydrate, NF | 0.20 |
| Pluroic F-127 | 0.10 |

Dissolving any one or a combination of the enzyme cleaning agent formulations of Examples 1-5 above, into any one or a combination of the multipurpose disinfecting agent solutions of Examples 6-8 above, will provide a solution for simultaneously cleaning and disinfecting contact lenses, wherein as discussed in detail below, the disinfection efficacy of the disinfecting agent is at least maintained.

The disinfection efficacy of the disinfecting agent in the working solutions of the present invention (enzyme plus disinfecting agent) was tested against a panel of other enzyme and disinfecting agent combinations presently sold in the marketplace including combinations representing examples from U.S. Pat. No. 5,096,607. The disinfection efficacy was measured by comparing the antimicrobial performance (log kill). See Table 1 below.

TABLE 1

| | MICROBIAL PERFORMANCE OF COLD CHEMICAL DISINFECTING SOLUTIONS | | | | | |
|---|---|---|---|---|---|---|
| PRODUCTS Antimicrobial Performance (log kill) | EXAMPLE 6 Disinfecting Agent Solution | EXAMPLE 2 Enzyme Plus EXAMPLE 6 Solution 1 tab/1.5 mL | OPTIFREE | OPTIFREE/ OPTIFREE ENZYME 1 tab/10 mL | RENU | RENU RENU-FIZZY 1 tab/10 mL |
| S.M. | | | | | | |
| 4 hr | 6.0 | 3.7–6.0 | — | — | 2.0–5.8 | 0.6–3.3 |
| 6 hr | 6.0 | 6.0 | 0.5–0.7 | 0.9–1.7 | 3.4–5.8 | 3.3–4.8 |
| 8 hr | — | — | 0.7–0.9 | 1.6–2.2 | — | — |
| S.E. | | | | | | |
| 4 hr | 4.5–6.0 | 4.0–6.0 | — | — | 2.1–5.8 | 2.3–5.8 |
| 6 hr | 6.0 | 6.0 | 3.5–6.0 | 3.2–6.0 | 5.0–5.8 | 3.0–5.8 |
| 8 hr | — | — | 6.0 | 6.0 | — | — |
| P.A. | | | | | | |
| 4 hr | 6.0 | 6.0 | — | — | 2.8–5.9 | 2.6–5.9 |

TABLE 1-continued
MICROBIAL PERFORMANCE OF COLD CHEMICAL DISINFECTING SOLUTIONS

| PRODUCTS<br>Antimicrobial<br>Performance<br>(log kill) | EXAMPLE 6<br>Disinfecting<br>Agent<br>Solution | EXAMPLE 2<br>Enzyme Plus<br>EXAMPLE 6<br>Solution<br>1 tab/1.5 mL | OPTIFREE | OPTIFREE/<br>OPTIFREE<br>ENZYME<br>1 tab/10 mL | RENU | RENU<br>RENU-<br>FIZZY<br>1 tab/10 mL |
|---|---|---|---|---|---|---|
| 6 hr | 6.0 | 6.0 | 3.0–3.6 | 0.7–1.2* | 3.8–5.9 | 3.3–6.0 |
| 8 hr | — | — | 3.2–3.9 | 1.1–1.6* | — | — |
| C.A. | | | | | | |
| 4 hr | 0.7–1.4 | 1.0 | — | — | 0.8–2.1 | 0–0.2* |
| 6 hr | 0.7–1.5 | 1.0–1.1 | 0–0.1 | 0–0.2 | 0.8–1.7 | 0–0.1* |
| 8 hr | — | — | 0.1 | 0–0.2 | — | — |
| | No effect on<br>disinfection efficacy. | | *Significant adverse effect on<br>disinfection efficacy. | | *Significant adverse effect on<br>disinfection efficacy. | |

For the working solutions of the present invention, the log kill as against S.M. did not significantly decrease at 6 hours, as against S.E. did not significantly decrease at 4 hours, as against P.A. did not significantly decrease at 4 hours, and as against C.A. did not significantly decrease at 4 hours. On the other hand, for Optifree and Optifree Enzyme (see below for composition), the log kill as against P.A. significantly decreased at 6 and 8 hours and for Renu and Renu-Fizzy (see below for composition), the log kill as against C.A. significantly decreased at 4 and 6 hours.

Standard culture methods, harvest and quantitative microbiological analysis techniques were used. The organisms used for this purpose were: *P. aeruginosa*, ATCC 15442; *C. albicans*, ATCC 10231; *S. marcescens*, ATCC 14041; and *S. epidermidis*, ATCC 17917.

Log kill was determined after 4, 6 and 8 hours' contact with the microorganisms using the standard method for log kill determination. See Pflug IJ, Holcomb RG, "Principles of Thermal Destruction of Microorganisms" in: Block SS, ed. *Disinfection, Sterilization, and Preservation*, 3rd ed., Philadelphia, Lea & Febiger, 1983:751–810; Houlsby RD, "An Alternative Approach for Preservative Testing of Ophthalmic Multiple-dose Products" *J. Parenter Drug Assoc.* 1980; 34(4):272–6; and Bruch MK, "The Regulation of Hydrophilic Contact Lenses by the Food and Drug Administration" *Dev. Ind. Microbiol*, 1976; 17:29–47.

The test results as expressed in terms of log kill are illustrated in Table 1 above.

Optifree, Optifree Enzyme, ReNu and ReNu-Fizzy are examples of antimicrobial agents and proteolytic enzymes which fall within U.S. Pat. No. 5,096,607 discussed previously. It is believed that Optifree, Optifree Enzyme, ReNu, and ReNu-Fizzy contain the ingredients set forth in Tables 2 and 3 below:

TABLE 2

| Ingredients | Solutions - Concentrations (w/v %) | |
|---|---|---|
| | Optifree[1] | ReNu Multi-Purpose[2] |
| Poloxamine 1107 | — | .5–1.0 |
| Sodium Chloride | .516 | .30–.49 |
| Citric Acid Monohydrate | .021 | — |
| Sodium Citrate Dihydrate | .56 | — |
| Boric Acid | — | .6–1.1 |
| Sodium Borate Decahydrate | — | .16–.4 |
| Disodium Edetate | .05 | .011–.11 |
| Polyquad[4] | .001 | — |
| Dymed[5] | — | .00005 |

TABLE 3

| Ingredients | Products - mg/tablet | |
|---|---|---|
| | Optifree Enzyme[3] | ReNu-Fizzy |
| Pancreatin | 40% Optizyme | — |
| Subtilisin A | — | 25 |

What is quite significant is that when the disinfecting agent solution of Example 6 is combined with the proteolytic enzyme of Example 2, the log kill is maintained substantially the same as if the disinfecting agent solution of Example 6 was not combined with the proteolytic enzyme of Example 2. Preferably the log kill does not decrease by more than 30%, more preferably by not more than 10% and preferably still, the log kill does not statistically decrease, and optimally does not decrease at all. Thus, the combination of the disinfecting solution and proteolytic enzyme has no significant effect on the disinfection efficacy of the disinfecting agent solution of Example 6.

On the other hand, when Optifree is combined with the Optifree Enzyme, the log kill substantially decreases from that of Optifree alone for *P. aeruginosa*. That is, there is a significant adverse effect on the disinfection efficacy of the Optifree disinfecting solution when it is combined with Optifree Enzyme.

Equally so, when ReNu disinfecting solution is combined with ReNu-Fizzy, the log kill of *C. albicans* significantly decreases and thus there is a significant adverse effect on the disinfection efficacy of ReNu when it is combined with the ReNu-Fizzy Enzyme.

With reference to Table 4 below, the effect of three enzyme compositions on the antimicrobial properties of the Solution of Example 6 was tested. The test results show that the enzyme composition of Examples 1 and 3 has no statistically detrimental effect on the antimicrobial properties of the Solution of Example 6. On the other hand, Enzyme Composition X shows a detrimental affect on the activity of the Solution of Example 6 against *C. albicans*.

TABLE 4

Averaged log-drops at the specified time intervals for Solution Example 6 with several enzymes (N = 2)

| ORGANISM | Time | Enzyme Composition X**** | Composition of Example 3** | Composition of Example 1*** | Solution of Example 6 Alone |
|---|---|---|---|---|---|
| S. marcescens ATCC 14041 | 2h | >4.7 logs | >5.1 logs | >5.3 logs | >5.1 logs |
|  | 4h | >4.8 logs | >5.3 logs | >5.3 logs | >5.3 logs* |
|  | 6h | >5.3 logs* | >5.3 logs* | >5.3 logs* | >5.3 logs* |
| S. epidermidis ATCC 17917 | 2h | >4.6 logs | >4.9 logs | >4.9 logs | >4.9 logs |
|  | 4h | >4.9 logs | >4.9 logs* | >4.9 logs* | >4.9 logs |
|  | 6h | >4.9 logs* | >4.9 logs* | >4.9 logs* | >4.9 logs* |
| S. aureus ATCC 6538 | 2h | 5.0 logs | 5.0 logs | 5.3 logs | 5.3 logs |
|  | 4h | >5.3 logs | >5.0 logs* | >5.3 logs* | >5.3 logs |
|  | 6h | >5.3 logs* | >5.0 logs* | >5.3 logs* | >5.3 logs* |
| P. aeruginosa ATCC 10231 | 2h | 4.2 logs | >5.0 logs | >5.0 logs | >4.8 logs |
|  | 4h | >5.0 logs | >5.0 logs* | >5.0 logs* | >5.0 logs* |
|  | 6h | >5.0 logs* | >5.0 logs* | >5.0 logs* | >5.0 logs* |
| C. albicans ATCC 10231 | 2h | 0.4 logs | 1.4 logs | 1.2 logs | 1.4 logs |
|  | 4h | 1.1 logs | 1.7 logs | 2.1 logs | 2.1 logs |
|  | 6h | 1.1 logs | 1.8 logs | 2.6 logs | 2.2 logs |

*Total Kill
**1 tablet/10 mL solution
***1 tablet/1.5 mL solution
****Enzyme Composition X consists of 0.4 Mg/Tablet Subtilisin A, [(Subtilisin A, 30 Au/g (Novo Industries of Copenhagen, Denmark)], 50.0 Mg/Tablet N-acetylcysteine, 6.0 Mg/Tablet Polyethylene glycol 3350, 43.0 Mg/Tablet Sodium carbonate - anhydrous, and 30.0 Mg/Tablet Sorbitol FG Instant.

Thus when the method of the present invention is used, the disinfection efficacy of the disinfecting agent is at least substantially maintained, preferably to meet or exceed the 1985 U.S. FDA guidelines for antimicrobial performance.

It should be appreciated to those of skill in the art that the present invention is not limited to the specific examples set forth above, and that many modifications and variations are within the scope of the present invention.

What is claimed is:

1. A method for simultaneously cleaning and disinfecting a contact lens, the method comprising the steps of:
   forming a disinfection solution comprising about 0.0001% polyhexamethylene biguanide, about 0.05% edetate disodium, about 0.37% sodium chloride, about 1.20% tromethamine, and about 0.025% tyloxapol;
   providing an effective and efficacious amount of subtilisin A in an amount of from about 0.0008 to 0.036 Anson units per single lens treatment, wherein when the subtilisin A is combined with the disinfection solution, the log kill against Pseudomonas aeruginosa and against Candida albicans at 4 hours does not significantly decrease;
   combining the contact lens, the disinfection solution and the subtilisin A; and
   soaking the lens in the resulting solution for a period of time sufficient to clean and disinfect.

2. The method of claim 1 wherein the log kill as against Pseudomonas aeruginosa and Candida albicans does not decrease by more than 30%.

3. The method of claim 1 wherein the subtilisin A is provided in the form of a composition selected from the group consisting of Composition A, Composition B, Composition C, Composition D, and Composition E,
wherein:

Composition A comprises about 0.00198 Au subtilisin A, about 40.0 mg Di-Pac, about 4.0 mg polyethylene glycol 3350 and about 4.0 mg povidone;

Composition B comprises about 0.00207 Au subtilisin A, about 40.0 mg Di-Pac, about 2.0 mg sodium carbonate, about 4.0 mg polyethylene glycol 3350 and about 4.0 povidone;

Composition C comprises about 0.012 Au subtilisin A, about 30.0 mg N-acetylcysteine, about 52.0 mg sodium carbonate, about 40.0 sorbitol FG, about 6.0 polyethylene glycol 3350 and about 7.0 mg tartaric acid;

Composition D comprises about 0.0003 Au subtilisin A, about 7.50 mg N-acetylcysteine, about 13.0 mg sodium carbonate, about 10.0 mg sorbitol FG, about 1.5 mg polyethylene glycol 3350 and about 1.75 mg tartaric acid; and Composition E comprises about 0.024 Au subtilisin A, about 6.00 mg N-acetylcysteine, about 10.40 mg sodium-carbonate, about 8.00 mg sorbitol FG, about 1.20 mg polyethylene glycol 3350 and about 1.40 mg tartaric acid.

4. The method of claim 3 wherein Composition A is selected.

5. The method of claim 3 wherein Composition B is selected.

6. The method of claim 3 wherein Composition C is selected.

7. The method of claim 3 wherein Composition D is selected.

8. The method of claim 3 wherein Composition E is selected.

* * * * *